United States Patent
Mendenhall

[19]

[11] Patent Number: 6,093,168
[45] Date of Patent: Jul. 25, 2000

[54] BREAST PUMP ATTACHMENT TO A HOUSEHOLD VACUUM CLEANER

[75] Inventor: Wade Mendenhall, Boise, Id.

[73] Assignee: OMW, Inc., Birmingham, Ala.

[21] Appl. No.: 08/489,021

[22] Filed: Jun. 8, 1995

[51] Int. Cl.[7] .................................................... A61M 1/06
[52] U.S. Cl. ............................................................ 604/74
[58] Field of Search ................................. 604/74, 75, 35, 604/36, 37, 38, 49, 54, 73, 93, 131, 133, 147

[56] References Cited

U.S. PATENT DOCUMENTS

| | | | |
|---|---|---|---|
| 3,782,385 | 1/1974 | Loyd | 604/74 |
| 4,772,262 | 9/1988 | Grant et al. | 604/74 |
| 4,964,851 | 10/1990 | Larsson . | |
| 5,071,403 | 12/1991 | Larsson . | |
| 5,127,411 | 7/1992 | Schoolman et al. | 128/863 |
| 5,295,957 | 3/1994 | Alda et al. . | |
| 5,304,129 | 4/1994 | Forgach . | |
| 5,358,476 | 10/1994 | Wilson . | |

FOREIGN PATENT DOCUMENTS 2126899  4/1984  United Kingdom ..................... 604/74

*Primary Examiner*—Manuel Mendez
*Attorney, Agent, or Firm*—Gerald M. Walsh

[57] ABSTRACT

A breast pump for extracting milk from a human breast includes a bell-shaped member that receives at least a portion of the female breast. A receiving container connects to the bell-shaped member that stores the milk after it has been extracted. The bell-shaped member also connects to an air conduit that is able to attach to an accessory hose from a household vacuum cleaner.

2 Claims, 5 Drawing Sheets

BREAST PUMP ATTACHMENT TO A HOUSEHOLD VACUUM CLEANER

BACKGROUND OF THE INVENTION

1. Field of the Invention

The present invention relates to a breast pump for extracting milk from a human breast and collecting the extracted milk in a receiving container. In particular, the present invention relates to a breast pump that can attach to an accessory hose from a household vacuum cleaner, thereby utilizing the vacuum cleaner pump as a suction source.

2. State of the Prior Art

Breast pumps are convenient for nursing mothers who require extracting their breast milk by artificial means which can be stored and later fed to the baby. They may also be required in some circumstances, for example, if the baby is temporarily unable to breastfeed, which can result in a loss of milk production in the breasts due to a decreased sucking stimulation. Breast pumps generally comprise a bell-shaped receiving device called a flange that attaches to the female breast and a milk receiving container that connects to the flange to temporarily store the milk after extraction. A vacuum source also connects to the flange to provide the negative pressure required to extract the milk. Different types of vacuum sources are commonly used in breast pumps, but most are either manually or electrically driven.

Manual breast pumps, including bulb, cylinder, and trigger pumps, are difficult to use because they require the active participation of the mother in squeezing or pulling a device to produce a momentary suction. Reports show that bulb pumps, due to the difficulty in sterilizing, harbor bacteria that can contaminate the expressed milk. Repeated manual pumping of these breast pumps is tiresome and requires exceptional strength in the hand and fingers. Furthermore, the suction produced is sometimes very weak which requires more time to extract the milk compared to some of the electrical pumps.

Electrically driven breast pumps are either battery or AC powered and are easier to use because they do not require active participation from the user to produce the suction. They have also been shown to express more milk that is higher in fat content compared to manual pumps. The basic types of electrically driven breast pumps are small air displacement and large air displacement pumps. Small air displacement electric breast pumps, such as the battery powered breast pumps, contain small motors that can take up to two minutes to generate their peak suction, therefore having a limited effectiveness in extracting milk. Large air displacement electric breast pumps, however, can generate their peak suction in less than a second, resulting in a nearly instantaneous suction and thus less time spent drawing milk. However, the large air displacement breast pumps are also the most expensive breast pumps available, and most are usually rented to mothers rather than purchased. Unfortunately, both types of electric breast pumps are much more expensive because the user must purchase the electric pump together with the flange and milk receiving container.

What is needed is a breast pump, preferably one comparable to the large air displacement breast pumps, that can be purchased separately from the suction source, thereby eliminating the user from having to purchase an expensive pump along with the flange and milk receiving container. Such a device will result in combining the efficiency and ease of use of the electric breast pumps with the affordability of the manual ones.

SUMMARY OF THE INVENTION

In view of the foregoing, it is therefore an object of the present invention to solve the problems described above of the conventional breast pump. More specifically, it is the object of the present invention to provide a breast pump that utilizes a household vacuum cleaner as the suction source. Another important object of the invention is to provide a breast pump that produces a nearly instantaneous suction. A further object of the invention is to provide a breast pump that requires minimal manual skill to operate. Another object of the invention is to provide a breast pump that allows the user to manually adjust the strength of the suction pressure.

The foregoing objects of the present invention are achieved by providing a breast pump which comprises a bell-shaped flange that receives at least a portion of the female breast. An adapter connects to the flange via an air path and functions as a cap to a receiving container that temporarily stores the extracted milk. An air conduit that is attachable to an accessory hose from a household vacuum cleaner also connects to the adapter. The vacuum cleaner produces an air suction condition that is in communication with the receiving container and bell-shaped flange via an air path provided by the air conduit and accessory hose.

The accessory vacuum cleaner hose connects to the air conduit providing suction to the container and bell-shaped flange. An air path connects the interior of the flange and the interior of the container to the air conduit in order to apply suction pressure to the breast.

In a preferred feature according to the present invention, the breast pump is provided with an air suction release mechanism to allow for adjusting the suction pressure on the breast. Preferably, the release mechanism is an aperture with a manually adjusted sliding cover that is located on the wall of the air conduit. The release mechanism could also consist of several holes located along the wall of the air conduit allowing the mother to cover some or all of the holes with her fingers during use to generate the optimal suction pressure.

In another feature according to the present invention, the adapter connects to the bell-shaped flange and also to the milk receiving container via an air path, thus allowing milk to flow from the breast through the flange and into the container. The adapter has a lower end with internal threads thereon. The milk receiving container, preferably a standard-sized baby bottle, has external threads on the upper end that engage the internal threads of the lower end of the adapter, thus being held secure by the adapter.

The air path extends between the interior of the bell-shaped flange and the upper end of the milk receiving container, and between the milk receiving container to the air conduit. The air path also extends from the air conduit to the accessory hose from the vacuum cleaner, thereby providing communication between the pump of the vacuum cleaner and the bell-shaped flange.

Other objectives, features, and advantages of the present invention will be apparent to those of skill in the art from the detailed description that follows taken in conjunction with the drawings, in which:

DETAILED DESCRIPTION OF THE DRAWINGS

Figure 1:
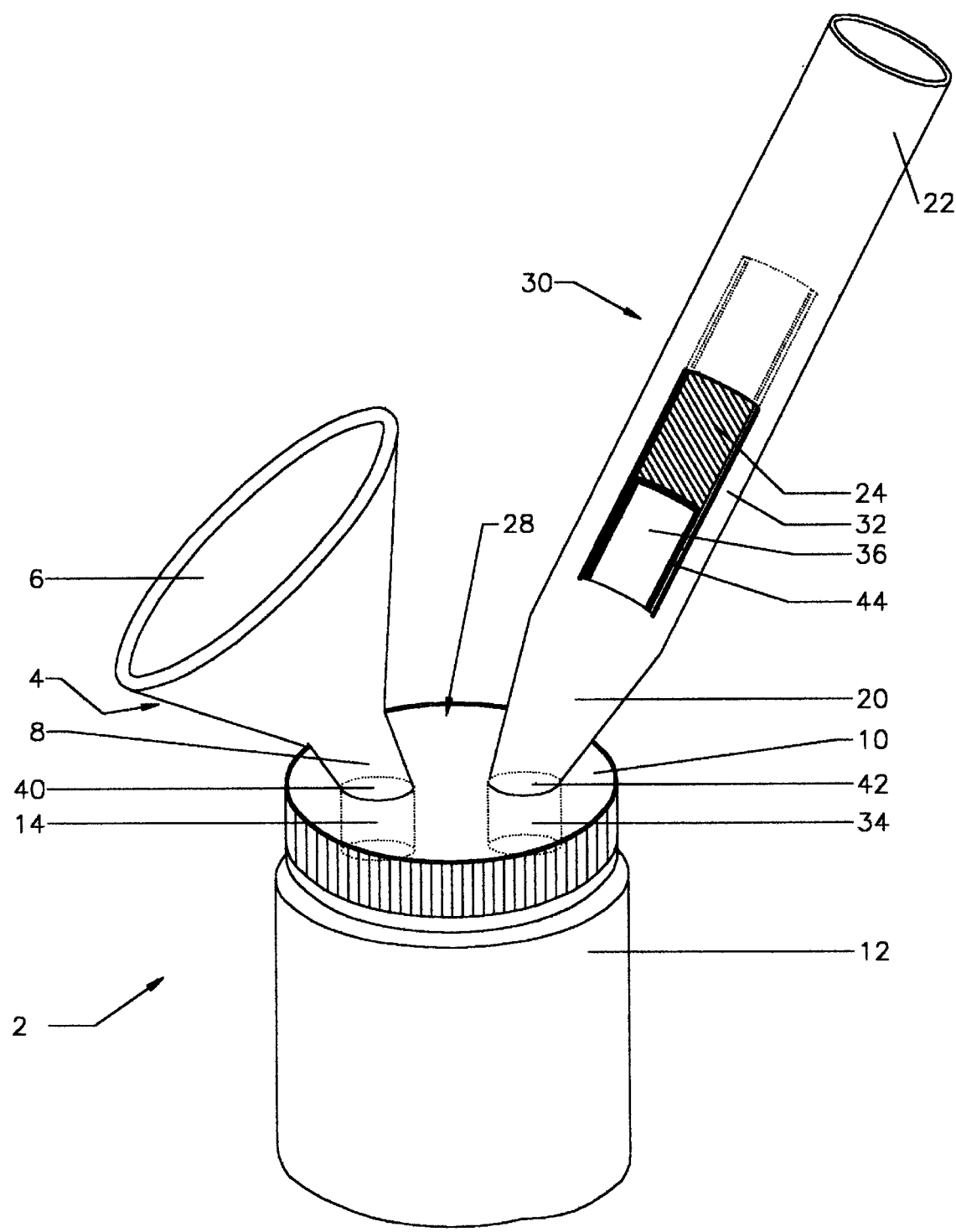
FIG. 1 is a perspective view of a breast pump made in accordance with the present invention.
Figure 2:
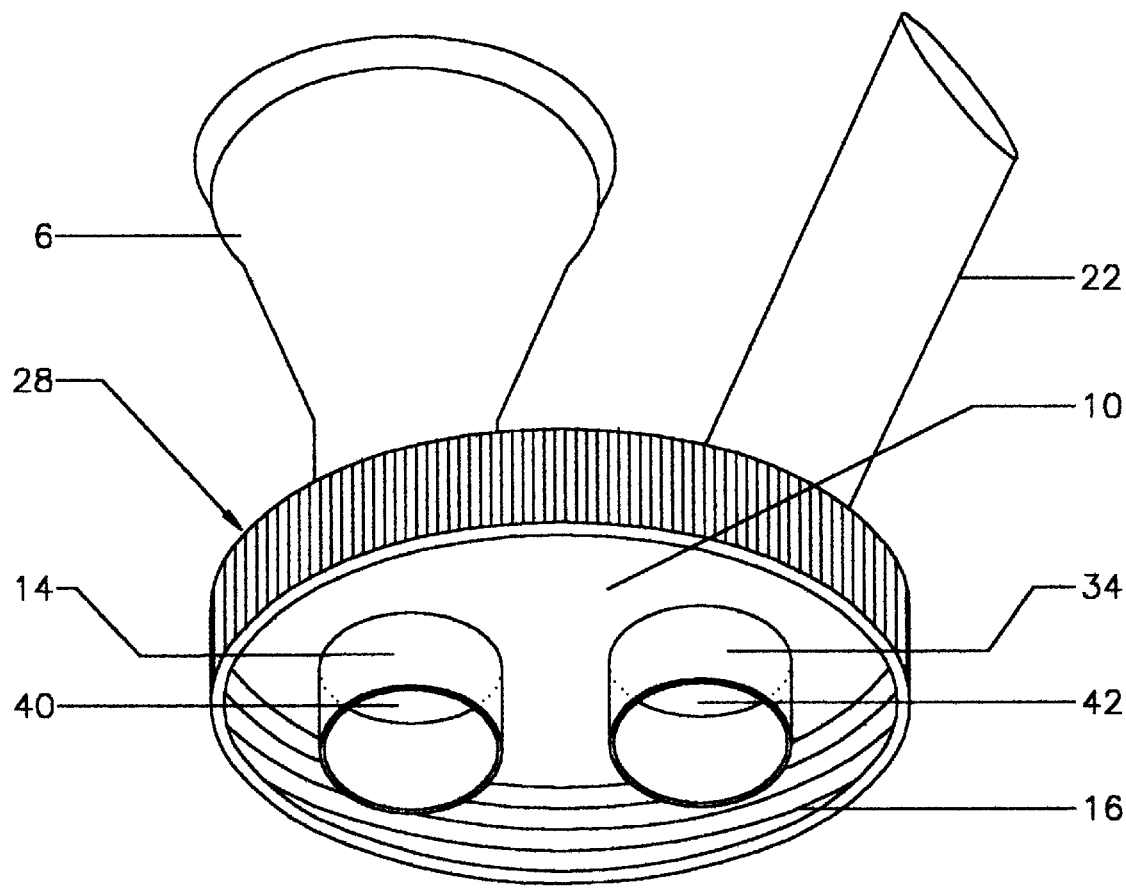
FIG. 2 is a bottom view of a breast pump with the container removed according to the preferred embodiment of the invention.
Figure 3:
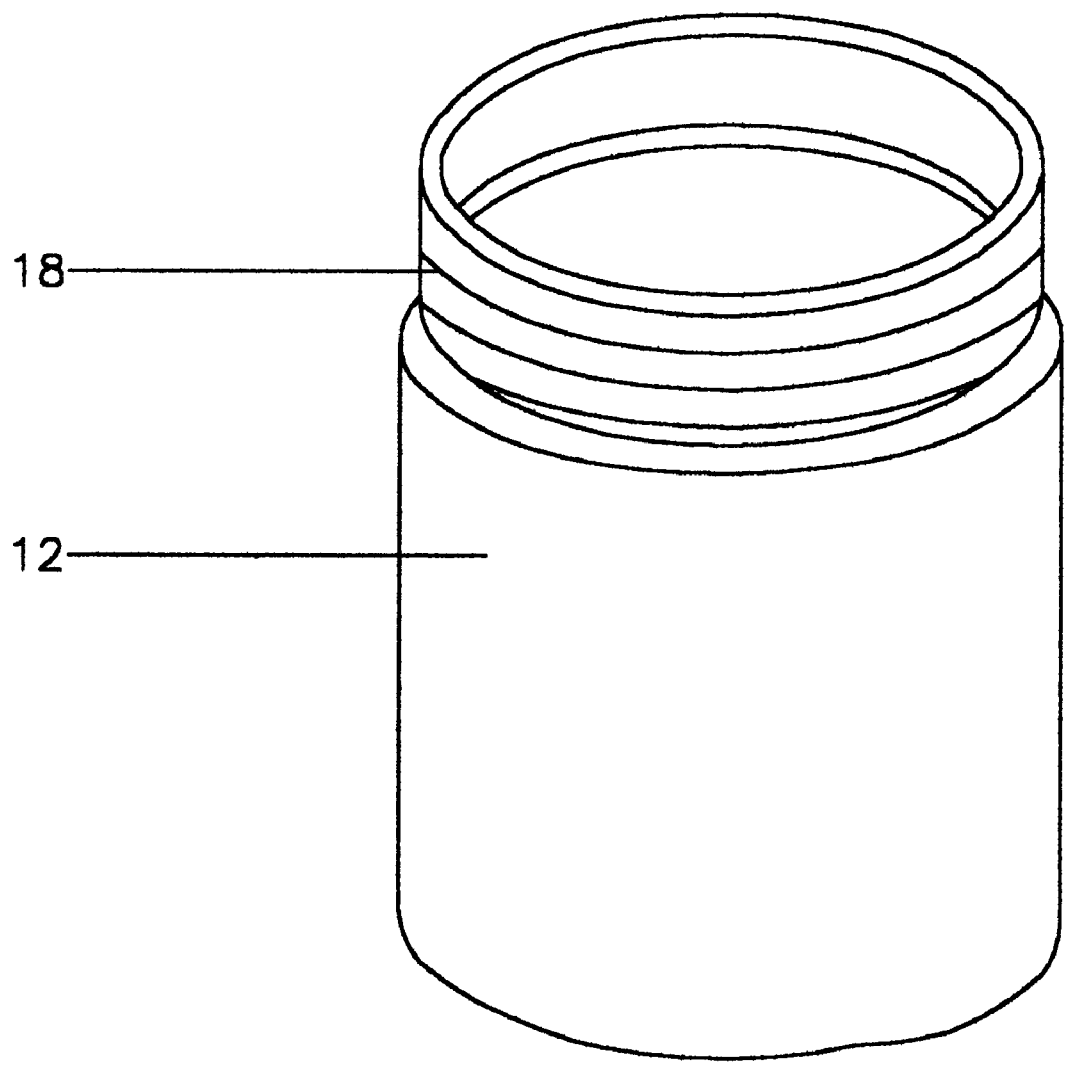
FIG. 3 is a front view of a container according to the present invention.

FIG. 1 illustrates a breast pump 2 constructed in accordance with the preferred embodiment of the current invention which includes a bell-shaped flange 4 that is held to a woman's breast to collect milk. The flange 4 includes a bell-shaped portion 6 that is held against the breast to form a seal and also a neck portion 8. The flange 4 has a large diameter at the bell-shaped portion 6 and tapers to a smaller diameter at the neck portion 8. The lower end of the neck portion 8 attaches to an adapter 28 around a hole 40 as illustrated in FIG. 2. The adapter 28 comprises a flat portion 10 and an internal annular threaded portion 16. A hollow, generally cylindrical first protrusion 14 of the neck portion 8 extends from the adapter 28 into a milk receiving container 12 approximately 1 to 5 millimeters. The acute angle formed between the flange 4 and the flat portion 10 of the adapter 28 is such that during use the container 12 can be held comfortably in an upright position. The upper end of the container 12 has an external annular threaded collar 18, as shown in FIG. 3. The internal annular threads 16 located at the lower end of the adapter 28 engage the external annular threaded collar 18 of the container 12.

Figure 4:
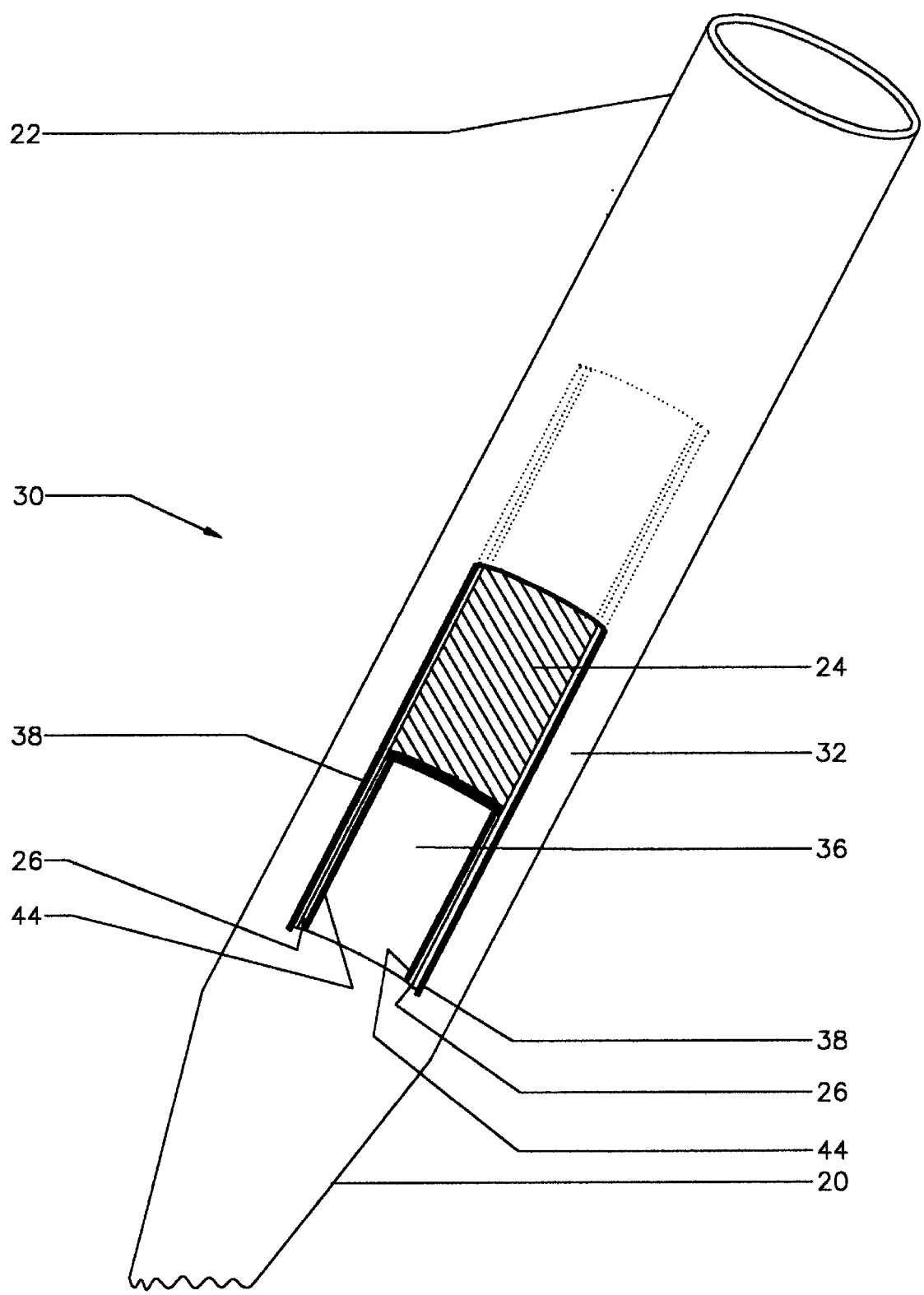
FIG. 4 is an exploded, fragmentary view of an air conduit according to the present invention.
Figure 5:
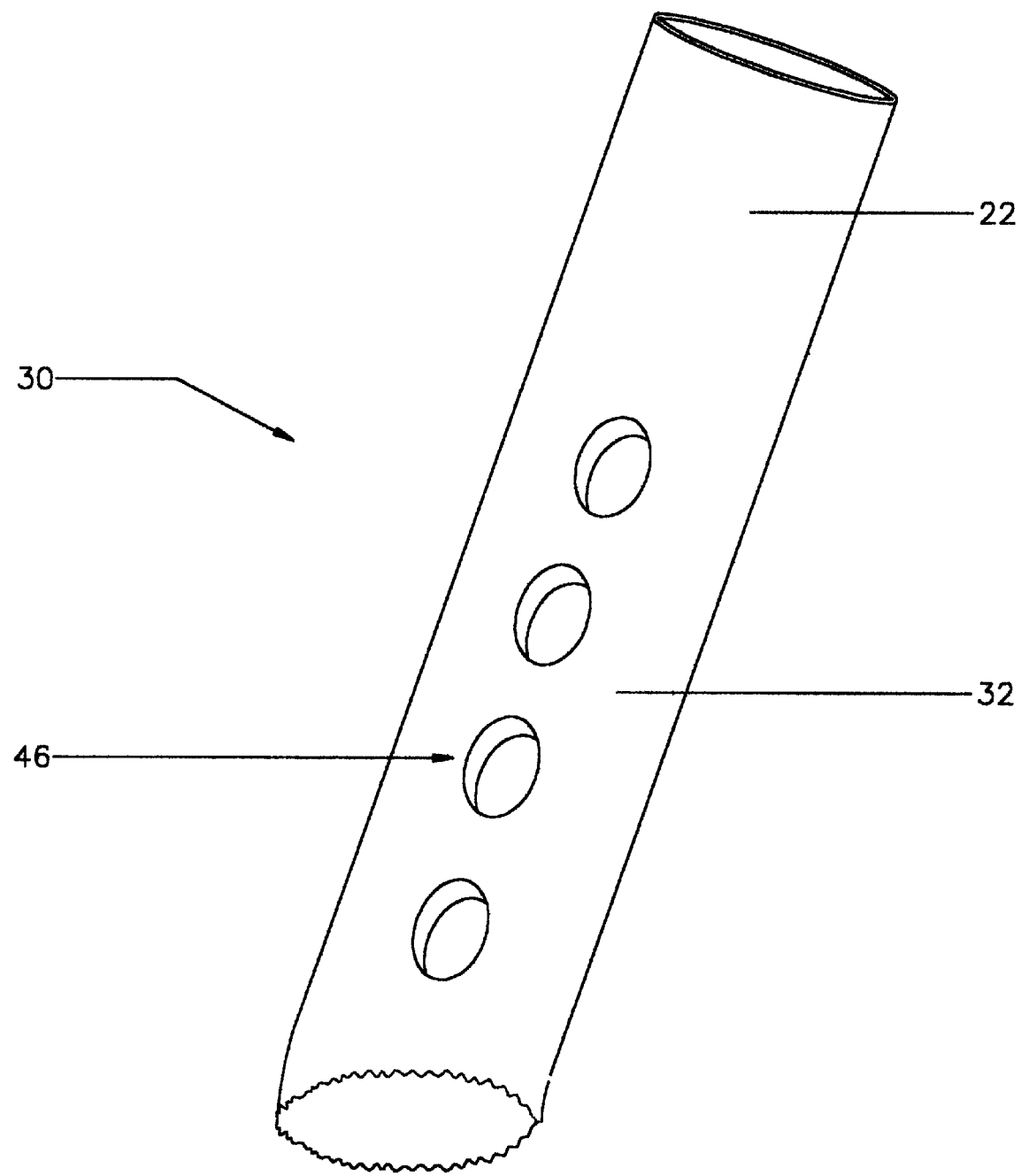
FIG. 5 is an exploded, fragmentary view of an air conduit according to a second embodiment of the present invention.

As shown in FIG. 1 and FIG. 4, an air conduit 30 includes a main body 32 and also a neck portion 20 at the lower end that attaches to the adapter 28 around a hole 42. The acute angle formed between the air conduit 30 and the flat portion 10 of the adapter 28 is such that extracted milk in the container is not drawn into the neck portion 20 of the air conduit 30 when the container 12 is held upright. A hollow, generally cylindrical second protrusion 34 of the neck portion 20 extends into the container 12 approximately 1 to 5 millimeters. The purpose of the protrusions 14 and 34 is to ensure the milk flows into the container 12 and is not drawn into the neck of the air conduit 20. The upper end of the main body 32 has an elongated portion 22 that can be inserted into an accessory hose from a household vacuum cleaner. The main body 32 of the air conduit 30 has an aperture 36 that is used as an air suction release mechanism. A short section of the wall of the aperture 36 consists of an outer lip portion 38 and an inner lip portion 44. A groove 26 fits between these outer and inner lip portions and houses a sliding cover 24. The sliding cover 24 extends snugly underneath a portion of the main body 32 as shown in FIG. 4. Outer lip portion 38 and inner lip portion 44 also extend underneath a portion of the wall of the main body 32 and function as a railing system for the sliding cover 24. By adjusting the sliding cover 24, the size of the aperture 36 changes, resulting in a decreased or increased suction pressure to the container 12 and bell-shaped flange 4. Suction pressure on the breast is maximized when the sliding cover completely covers the aperture. However, when the aperture is fully open, most of the suction pressure is lost, resulting in minimal suction pressure. FIG. 5 illustrates a second embodiment of the suction release mechanism according to the present invention which includes a plurality of holes 46 located in the main body 32 of the air conduit 30. One or more of the holes 46 are covered by the user's fingers during use to allow outside air to rush in, therefore decreasing the pressure in order to generate the optimal suction pressure on the breasts.

From the description of the apparatus, it is believed that the operation of the present invention is apparent. The bell-shaped portion 6 of the flange 4 surrounds at least a portion of the female breast, including the nipple, in order that the breast is received within the interior of the bell-shaped portion 6. Air suction pressure produced by the household vacuum cleaner is in fluid communication with the bell-shaped flange 4 by an interconnecting air path. Air is drawn in from the flange 4 through the adapter 28 and first protrusion 14 into the container 12, through the second protrusion 34, the air conduit 30, accessory hose, and finally into the vacuum pump. Suction pressure on the breast is such that the skin forms a seal with the bell-shaped portion 6 in order to draw out the milk. Suction pressure is regulated by moving the sliding cover 24 to increase or decrease the size of the aperture 36 to provide a comfortable suction pressure on the breast. Extracted milk flows through the neck portion 8 of the flange 4, through the adapter 28 and first protrusion 14, and falls into the container 12 where it is temporarily stored.

In the preferred embodiment, flange 4, air conduit 30, and adapter 28 are made from a hard plastic material that does not bend under the pressures generated during use. However, flange 4 may also be made from a soft silicone-type material that is more pliable and which may form a tighter seal with the breast. In the preferred embodiment, container 12 is made from plastic or glass. It could, however, be made from any other type of material that is insoluble in breast milk.

The present invention thus provides a breast pump that can attach to an accessory hose from a household vacuum cleaner thereby generating peak suction almost instantaneously, resulting in limited time spent drawing milk from the breast. The invention also provides a breast pump that is very economical compared to electrical breast pumps as the user can purchase the flange and milk receiving container separate from the electric pump. The breast pump requires minimal manual skill to operate and also allows the user to manually adjust the strength of the suction pressure.

Although the present invention has been described with many specificities, these should not be considered a limitation but rather as exemplification of the invention. Various other modifications can be made without departing from the spirit and scope of the invention. For example, the flange 4 may be made of a soft silicone-type material which is pliable to possibly provide a more comfortable fit, or it may be made of a hard plastic material, such as plastic, to avoid the pinching that has been reported to occur with the soft material. Protrusion 14 and protrusion 34 may project straight down into the container 12 as shown, or they may curve to one side or the other. Furthermore, the elongated portion 22 of the air conduit 30 may be of varying diameters and lengths to accommodate different sized accessory hoses from different vacuum cleaners.

Those skilled in the art will understand that further modifications may be made to the described specifications and illustrations and still fall within the scope of the invention as claimed.

I claim:

1. An apparatus for pumping breast milk comprising:
   (a) a suction bell having a flared end, adapted to surround a nipple and a portion of a female breast, and an opposite end in fluid communication with an adapter, said adapter having an internal threaded portion;
   (b) an air conduit having one end in fluid communication with said adapter and an opposite end in fluid communication with a hose on a vacuum cleaner; and
   (d) a container having an externally threaded portion that can engage said internal threaded portion of said adapter, said container having an interior space in fluid communication with said suction bell and said air conduit;

Wherein
   said air conduit contains an aperture having a sliding cover mechanism permitting manual opening and closing of said aperture to varying degrees from completely closed to completely open by sliding said cover in a forward or backward direction, whereby
   suction pressure is transmitted from said vacuum cleaner to said air conduit to said container to said suction bell to said breast and nipple thereby expressing milk from said breast and nipple into said container, and whereby
   said suction pressure is varied with desired frequency and magnitude by opening or closing said aperture with said sliding cover.

2. An apparatus for pumping breast milk according to claim 1 wherein said aperture in said air conduit has inner and outer lip portions with grooves in between forming a railing system for said sliding cover.

* * * * *